United States Patent [19]

Spinello

[11] Patent Number: 4,992,217
[45] Date of Patent: Feb. 12, 1991

[54] APPARATUS AND METHOD FOR STERILIZING, DESTROYING AND ENCAPSULATING MEDICAL IMPLEMENT WASTES

[76] Inventor: Ronald P. Spinello, 523 Post Ave., Westbury, N.Y. 11590

[21] Appl. No.: 364,978

[22] Filed: Jun. 9, 1989

[51] Int. Cl.⁵ .............................. A61L 11/00
[52] U.S. Cl. .................... 264/0.5; 252/628; 422/294; 422/307
[58] Field of Search ............ 209/930; 252/628; 264/0.5; 422/22, 294, 307; 424/1.1; 427/4, 331; 523/129; 524/1

[56] References Cited

U.S. PATENT DOCUMENTS

| | | | |
|---|---|---|---|
| 3,476,506 | 11/1969 | Andersen et al. | 422/294 |
| 3,892,706 | 7/1975 | Jetzer | 523/129 |
| 4,409,029 | 10/1983 | Larker et al. | 264/0.5 |
| 4,434,074 | 2/1984 | Fox et al. | 252/628 |
| 4,662,516 | 5/1987 | Baker, Sr. et al. | 206/363 |

Primary Examiner—Charles T. Jordan
Assistant Examiner—Richard W. Wendtland
Attorney, Agent, or Firm—Hoffmann & Baron

[57] ABSTRACT

Apparatus and method for sterilizing and encapsulating contaminated waste particularly medical implement waste in which a volume of thermoplastic compound having a melting point temperature-calibrated at a value which corresponds substantially to the temperature at which all biological contamination is rendered sterile substantially on contact, and impregnating a space containing contaminated waste items with the liquid compound and thereafter cooling the mass to its solidified phase while containing it against protrusion of any waste item.

20 Claims, 5 Drawing Sheets

FIG. 11
FIG. 12
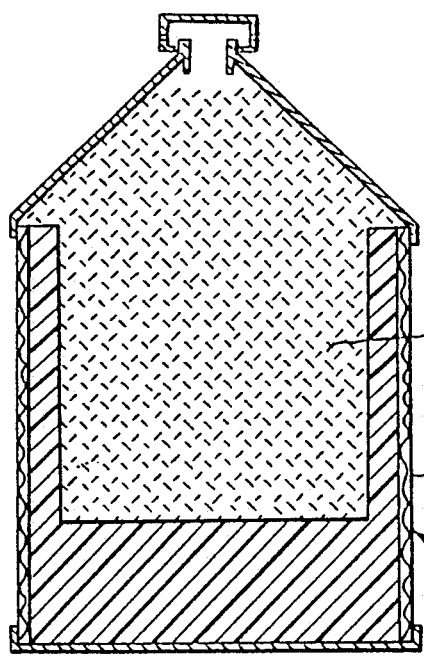
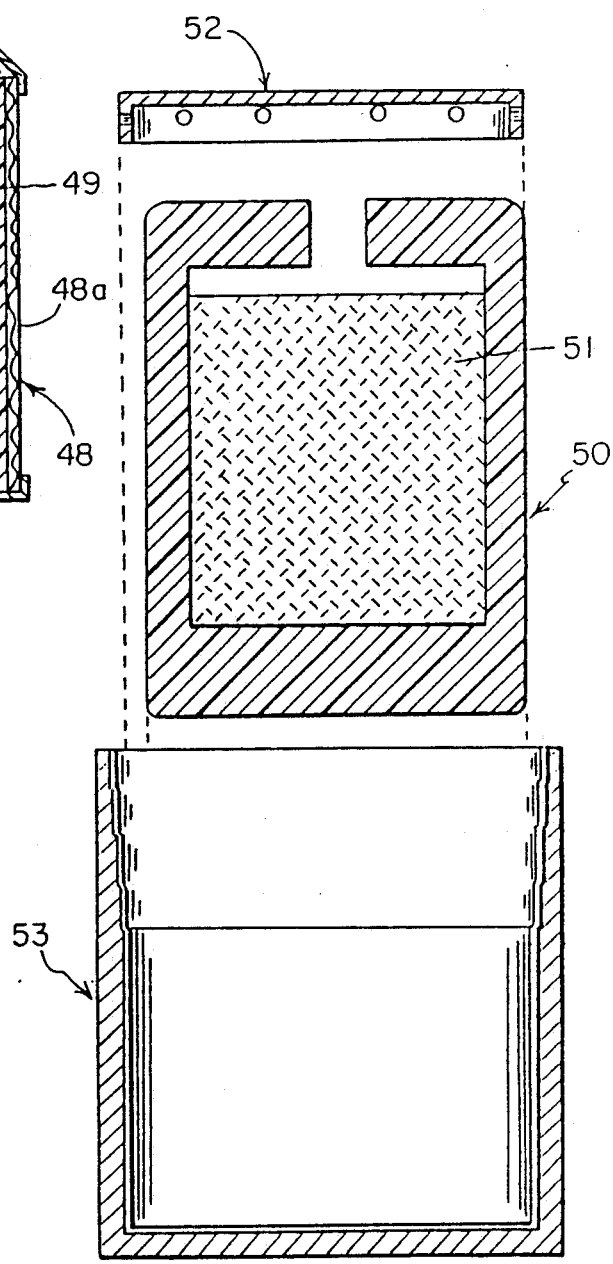

APPARATUS AND METHOD FOR STERILIZING, DESTROYING AND ENCAPSULATING MEDICAL IMPLEMENT WASTES

The invention is directed to safe handling and disposal of hazardous waste such as medical implement waste from hospitals, health care facilities and dental and medical offices. It is particularly concerned with safely processing contaminated needles, scalpels and like sharp metal objects which have invaded the human body, as well as used hypodermic syringe barrels and glass vials, all of which are difficult and dangerous to handle, destroy or eventually store.

BACKGROUND OF THE INVENTION

Environmental protection laws at all levels of government are concerned with contaminated medical wastes. In most jurisdictions of the civilized world such wastes can no longer be put in the conventional channels of waste disposal. Nor can much of such wastes be reliably rendered safe in a practical, discernible way at the point of use. On-site sterilization, for example, of many medical implements is giving way to the use of disposable implements because sterilization is labor-intensive, subject to human error and all but impossible to verify. Used hypodermic syringes are possibly the most dreaded waste of all because they are inherently contaminated and dangerous to handle; they resist decay and can float on an ocean until a shore is found. And they are sought by the illicit drug trade.

Until recently medical facilities were required to shear off the needle part from the syringe body immediately after the injection, but this procedure was found to spread disease by means of the air-borne aerosols generated by the mechanical shearing action. Also, the sharp, contaminated needle tip remained to be handled and disposed of. Current regulations call for dropping the contaminated syringe with needle intact into a safe container, called a "sharps" box, for custom delivery to an authorized repository.

A state of the art device destroys the needle at the point of use by passing a large current at low voltage through the needle to reduce it and all attendant contaminants to a minute, sterile, incinerated residue. That invention protects the nearby medical personnel and the environment but it cannot cope with scalpels, glass or the left over hollow barrels of the syringes. Thus the medical facility, while performing a useful service to itself and society, is left with its other contaminated "sharps" and syringe bodies to ship to a safe repository. For its otherwise good efforts it has saved neither time nor cost. There is also in the prior art a technique for rendering sharp items less dangerous by potting in resin such as epoxy using a hardener. Encapsulated spores can, however, survive for years and the system is regarded as unsafe for lack of sterilization.

The present ground rules for dealing with medical instrument wastes not destroyable safely on the site call for: (1) minimum handling at the point of use, that is the person performing the injection, for example, is expected to drop the used syringe directly into the "sharps" box; (2) containerizing the waste by means of a sealed "sharps" box marked "hazardous", and (3) logging and shipping the containerized, contaminated waste to a special repository under an umbrella of costly manifests which must circulate among the facility, the hauler and the repository and then kept available for audit for several years. The expense to society is enormous and the beaches of the world reveal the flaws in the system.

The present invention is a fresh attempt to solve the problems. Its objects and features are:

to provide a relatively inexpensive container to receive the medical instrument waste at the point of use, to provide a way to sterilize inexpensively the contaminated contents within the container while still at the medical facility, to render the syringe bodies in the container not only unusable but unidentifiable, to render the needles, the scalpels and the glass harmless against cutting or piercing personnel and to render them unrecoverable by any practical means, to provide a containerized sterilizing system which is reliable and virtually immune to human error, to provide a containerized sterilizing system which clearly indicates even to the casual observer whether the contents have been rendered harmless and safe, to provide a containerized medical implement waste disposal system in which neither the treated container nor its contents can float, to provide a reliable, relatively inexpensive method and apparatus to treat contaminated medical implement wastes at the point of use in a manner which renders them capable of being thrown out in the ordinary channels of waste disposal, and to provide a containerized sterilizing system for medical implement waste which if desired lends itself to recycling.

BRIEF SUMMARY OF THE INVENTION

In accordance with the invention a container similar in size and shape to existing "sharps" boxes is formed of a material having a high melting point and is provided with a lower portion containing a predetermined volume of a temperature-calibrated thermoplastic compound forming a stable, rigid base. The melting temperature of the compound is selected at a value at which sterilization of biological contamination is effected virtually upon contact. Used medical implement waste such as hypodermic needles, scalpels, glass vials and hypodermic syringes, with or without the needles, are accumulated in the container in the conventional manner. The full container is heated by appropriate means such as an oven to a temperature above the melting point of the temperature calibrated compound. When the compound liquifies pressure is applied to cause the hot liquid to flow into the space containing the preheated waste products, to flow over and around all bits and pieces and to fill all void spaces. The container is vented at the top and the flow continued preferably until the liquefied compound appears at the top. All biological life has then been killed.

In a preferred embodiment, the container is collapsible from the bottom up to eliminate the space where the compound was originally stored. It is this feature which provides an error-free, highly conspicuous indication that the sterilizing and encapsulating steps have occurred within. If desired, the outside of the container can be color and word coded to show the hazardous made before the container is reduced in size and the safe mode thereafter.

The container is held in its reduced-size condition until the compound has cooled and hardened to encapsulate and shield all sharp points and edges and to lock the container in its new geometry. Glass vials, if not broken upon insertion can be broken by the pressure, and the plastic of which disposable syringe bodies are made, having a melting temperature substantially below that of the compound, will be reduced to an amorphous, void-free mass. Thus there are no visually identifiable or usable syringe parts remaining in the final mass. The container is now hazard-free and can be disposed of in the conventional channels of waste disposal either at a land fill or an incinerator. It is also capable of recycling to retrieve the compound and the metals of which the medical implements were made, should such be desirable for any reason.

BRIEF DESCRIPTION OF THE DRAWINGS

FIG. 11 is a view in vertical section of another embodiment of the invention; and FIG. 12 is a view in vertical section showing another embodiment of the invention using a separate potting container.

DESCRIPTION OF THE PREFERRED EMBODIMENTS

Figure 1:
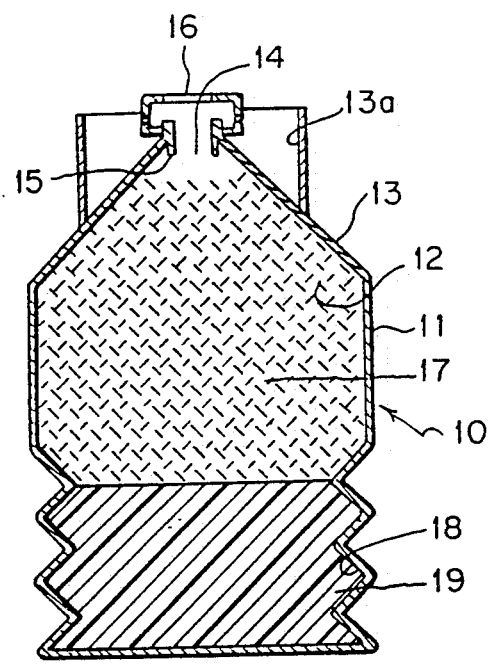
FIG. 1 is a view in side elevation of a waste container formed in accordance with the invention and prior to the sterilization and encapsulating steps.
Figure 2:
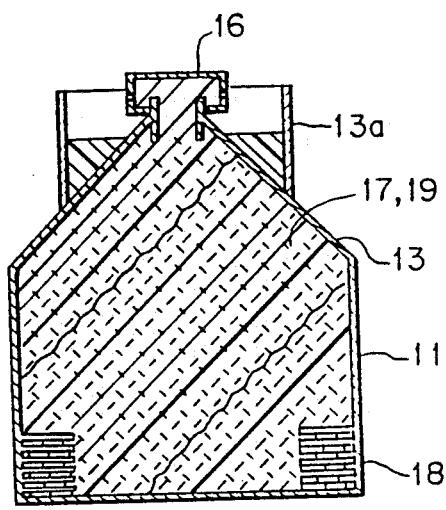
FIG. 2 is a view in side elevation after the sterilizing and encapsulating steps.

Referring to FIGS. 1–4 the invention is illustrated as embodied in a container 10 formed of a heat and puncture resistant material such as high melting point plastic, of which nylon and teflon are examples and which can be reinforced, or of metal. The container 10 is cylindrical and includes a rigid upper portion 11 defining a chamber or space 12 to receive waste implements such as hypodermic needles, glass vials, scalpels and like wastes produces which in the medical and dental professions are now known as contaminated "sharps". Syringe bodies, with or without the needles attached, can also be included, such typically being of the single-use, disposable type formed of thermoplastic. The upper portion 13 of the container is preferably convergent to form a relatively small waste-receiving opening 14 having a depending cylindrical wall 15 and closed by a detachable vented cap 16.

The lower or base portion of the container comprises a collapsible storage space 18 containing a thermoplastic medium 19 which is temperature calibrated as to its melting point selected to achieve sterilization of all known biological micro-organisms including vegetative bacteria, viruses and spore forms. A typical material for this purpose which is relatively harmless to the environment is linear, hydroxy terminated copolyester synthetic resin which can be formulated to afford full flow viscosity at temperatures from 160° C. to in excess of 260° C. Such products do not vaporize or generate toxic fumes until temperature in excess of 300° C. are reached. They are marketed for other purposes under such trademarks as dynapol and Jet-Melt.

Most medical researchers studying the effects of heat as a means of sterilizing refer to a temperature coefficient model in which death of the mirco-organisms being studied (death time) is plotted as a function of time and temperature. Research strongly indicates that no known micro-organisms can survive temperatures in excess of 160° C. for longer than a fraction of a minute. See "Disinfection, Sterilization and Preservation", by Seymour S. Block, Lea & Febger, 1983. It should be understood however that there is a given range of times and temperatures below 160° C. which effectively kill all known micro-organisms. It is therefor possible to design systems whereby plastics having melting temperatures less than 160° C. are allowed to remain in contact with the micro-organisms for time consistent with the death times of the organisms. The preferred embodiment however makes use of plastics having temperatures high enough to kill the micro-organisms substantially on contact, and thereby provides a fail-safe degree of overkill. Also, the system of the present invention provides an inherent time constant representing the time for the liquid phase thermoplastic to revert during cooling to its solid final phase without requiring a timing function subject to human error.

In dry gaseous media such as hot air having relatively lower specific heat characteristics, either higher temperatures or measurable time constants for heat exposure come into play. In the preferred embodiments of the present invention, liquid phase contact at temperature achieving rapid death to all biological contaminants in their most heat-resistant form, i.e. the spore form, is desirable because it eliminates the possibility of human error in the operation of the system and renders the successful operation visually discernible at a glance from a substantial distance, all of which are vital in policing the environment for human life-endangering contamination.

The appearance of the thermoplastic material at the vented cap will indicate that the entire space 12 has been impregnated with molten plastic. To provide for the possibility that the displacement factor of the waste items in the space 12 will have a range of values a surplus of thermoplastic can be provided together with an overflow reservoir 13a in the form for example of a visible, open cup surrounding the cap. To accommodate a situation in which the waste items 17 only partially fill the space 12 the conical upper portion 13 can be made collapsible under pressure int he encapsulating phase as described below.

The temperature-calibrated thermoplastic medium 19 in the embodiment of FIGS. 1–4 is illustrated as solid although it can take the form of particular matter or granules. To hold the granules in place prior to melting a covering screen or perforate cover (not shown) can be secured to the container above the material.

The wall of the base portion 18 of the container is made collapsible by corrugation or accordion pleating locked in its open position (FIGS. 1 and 3) by the solid phase of the thermoplastic medium 19 and also locked in its collapsed position (FIGS. 2 and 4) by the same medium. If it is desired to make the container self-actuating (in the presence of heat) the collapsible wall can be made resilient with its stable or rest position collapsed. To this end a coiled tension spring (similar to the spring 37 in FIGS. 5 and 6) can be included inside or outside the container if additional force is required. Additional force can also be derived from the use of heat shrinkable plastic in the container walls either on the x or the y axis or both.

Figure 9:
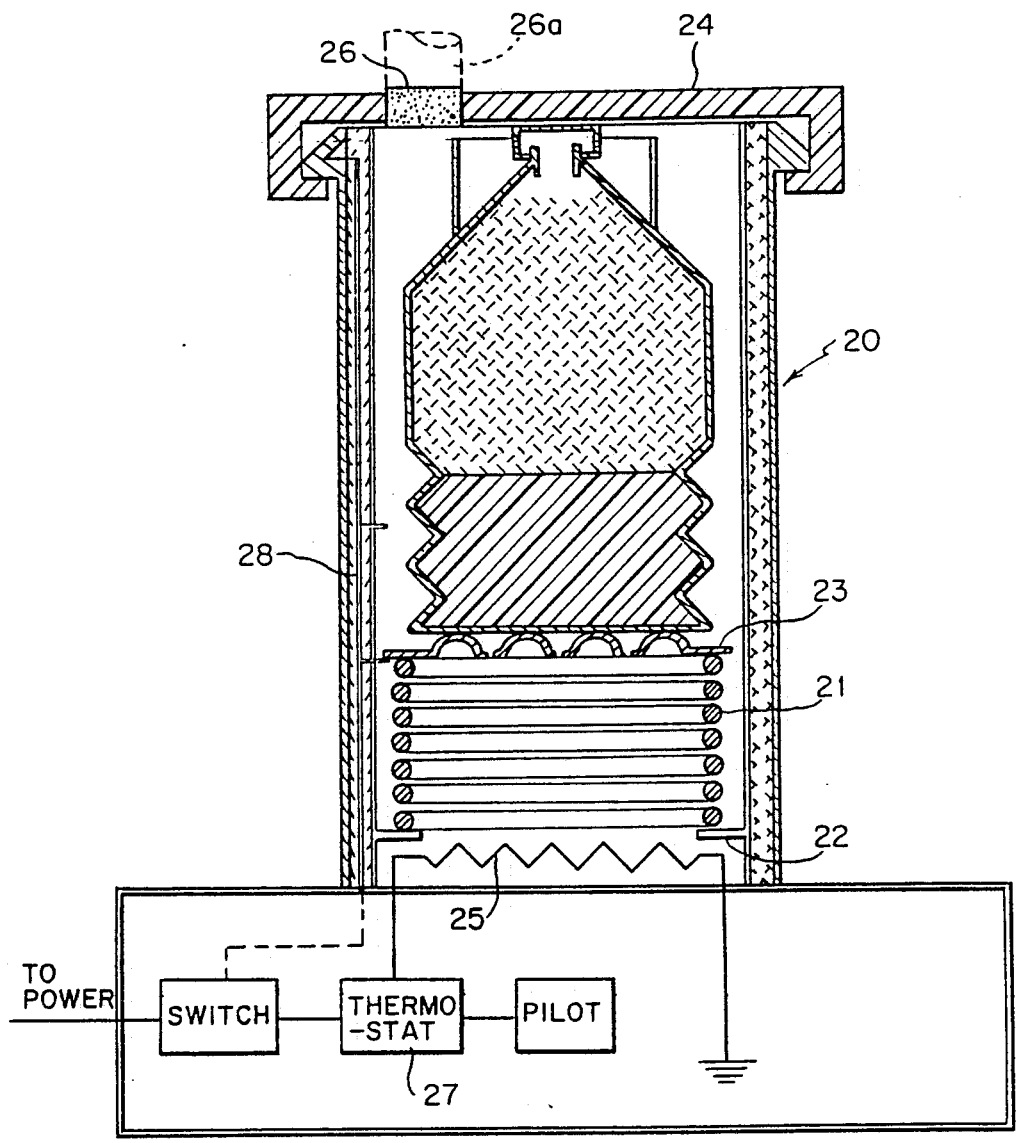
FIG. 9 is a view in vertical section of an oven containing a filled container corresponding to that of FIG. 3 and capable of carrying out the sterilizing and encapsulating functions.
Figure 10:
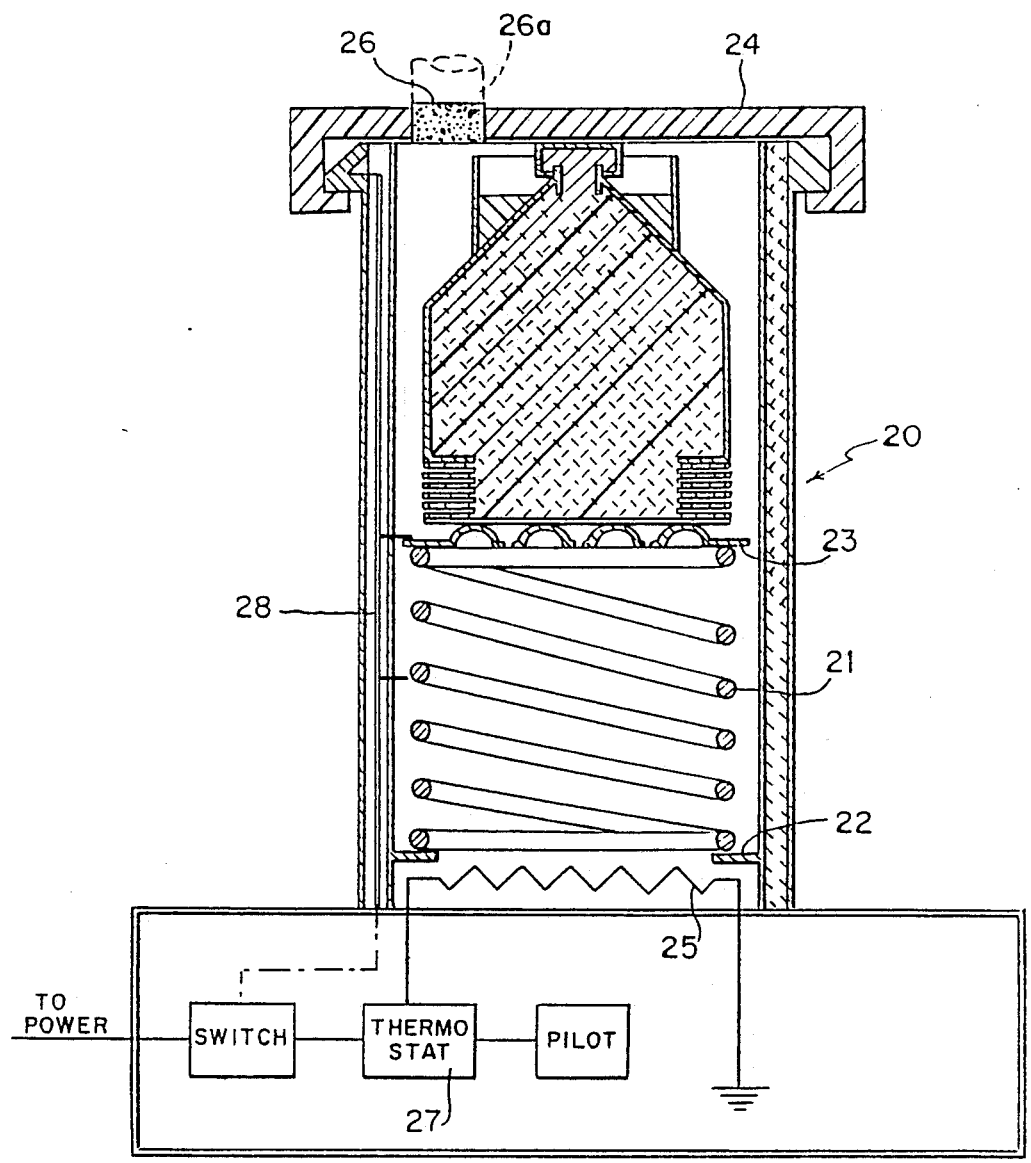
FIG. 10 is a view in vertical section of the oven corresponding to FIG. 9 but showing the container after sterilization and encapsulation.

The sterilizing and encapsulating action in the illustrated embodiment are carried out by a special oven 20 shown in FIGS. 9 and 10 which provides the forces necessary to compress the container. The over 20 includes a compression spring 21 resting on a support 22 and carrying a perforated, corrugated plate 23 on which the filled container 10 (FIGS. 1 and 3) is seated. The spring 21 is compressed by the closed oven cover 24 pressing down on the container cap 16. A resistance heater 25 energized from the mains through a switch and thermostat 27 provides the controlled heat to liquefy the temperature-calibrated thermoplastic mass 19. As heat is applied, below the level to harm the container and above the level to liquefy the thermoplastic, melting will gradually occur at which time the liquefied thermoplastic at a temperature pre-selected to destroy the biological contaminants in the waste items 17 will begin to flow into the interstices around the preheated bits and pieces of waste in the space 12.

The biological contaminants are destroyed substantially upon contact and all sharp edges and points become encapsulated. Also, the collapsible bottom 18 of the container will compress, thereby changing the geometry and appearance of the container. Gaseous by-products vent from the cap 16 and through a suitable filter 26, including charcoal, for example in the cover 24 of the oven and, if desired an evacuation conduit 26a. Alternatively, or in addition the oven can be vented to the outside air, as is conventional in autoclave operation. The cooled container is thus rendered hazard-free and can be discarded in the conventional channels of commerce by conventional carriers. Thermoplastic syringe bodies in the container melt at temperatures below the calibrated temperature and are, therefore, melted down and destroyed as an unstable, irretrievable, unrecognizable part of the sterile, amorphous mass.

The oven 20 can be operated by a position sensing switch actuator 28 which is activated by the carrier plate 23 to initiate heating when the plate is lowered and to terminate heating when it lifts (FIGS. 9 and 10). The actuator can also be coupled to the cover 24 to release a latch when the heating cycle is completed. The cover can be spring biased to an open position when released to hurry the cooling cycle, and residual compression in the spring 21 can expose more of the container to the atmosphere and also position it to be easily manually removed.

Figure 3:
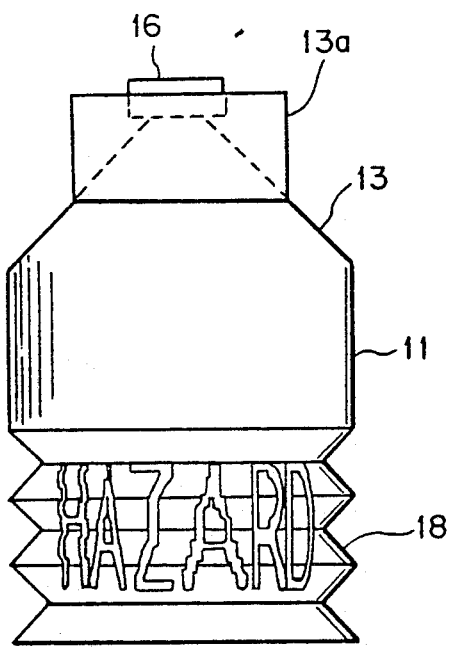
FIG. 3 is a view in vertical section of the waste container as shown in FIG. 1 showing the container filled with hazardous medical implement waste.
Figure 4:
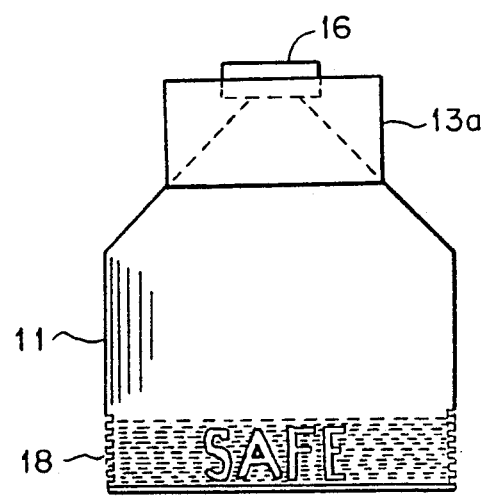
FIG. 4 is a view in vertical section of the waste container as shown in FIG. 2, after sterilization and encapsulation of the waste.

The thermoplastic mass, when cooled, locks the container in its compressed condition to mark its sterile non-hazardous condition. If desired, as best seen in FIGS. 3 and 4, the concave or depressed portions of the base can be color coded in red to indicate the hazardous state and a word to that effect can be included. The outer edges can be marked so that when compression has occurred the word "safe" appears and the hazard indicator disappears. Because the thermoplastic mass 19 has been selected for a melting temperature close to or above that which sterilizes on contact, the system becomes error proof and visually verifiable. It will be understood that a certain margin for error is built into the system in that a finite time factor for killing by heat is inherent in the system representing the time for cooling down to the solid plastic. Thus it is not essential that the temperature of the thermoplastic liquid actually reach that which kills instantaneously, although it is preferred where possible to establish safety factors using both elevated temperatures as well as any time factor which is inherent in the time required for the temperature of the thermoplastic to drop to that at which the solid phase occurs.

Figure 5:
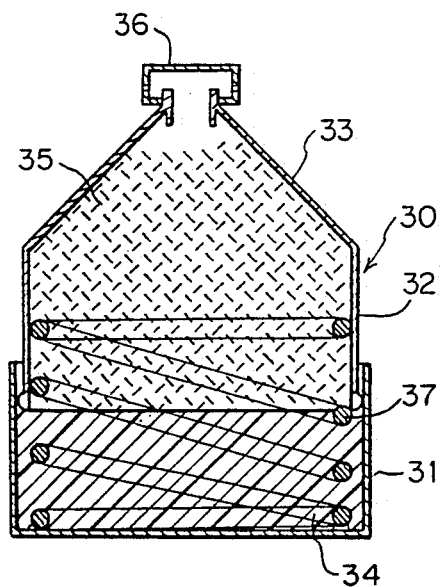
FIG. 5 is a view in vertical section of another embodiment of the invention prior to sterilization and encapsulation.
Figure 6:
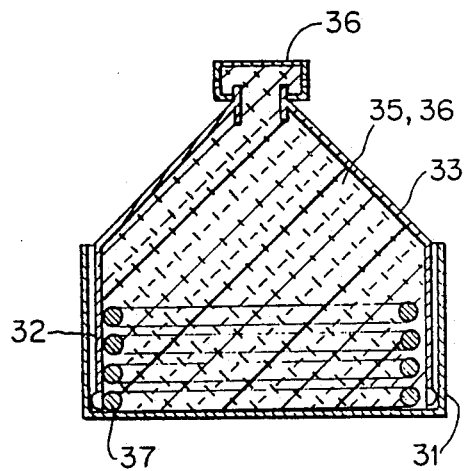
FIG. 6 is a view in side elevation of the unit of FIG. 5 after sterilization and encapsulation.

Referring to FIGS. 5 and 6 another embodiment of the container is disclosed in which the container 30 is formed of telescoping base and top sections 31 and 32, respectively. As in the embodiment of FIGS. 1–4, the upper part 33 of the top section 32 is conical. Normally solid phase thermoplastic 34 fills the base 31 with waste items 35 filling the upper section, shown closed by a vented cover 36. If desired the two telescoping sections can be linked by a coiled tension spring 37 joined at its top to the section 32 and its bottom to the base section 31. The container is adapted to be placed in an oven similar to that of FIGS. 9 and 10 to liquefy the thermoplastic and thereby set up the sterilizing and encapsulating functions, resulting in the configuration of FIG. 6. Hazard warnings in the cylindrical part of the upper section will, appropriately, be obscured by the lower section. It will be understood that heat destroyable warnings can also be used.

Figure 7:
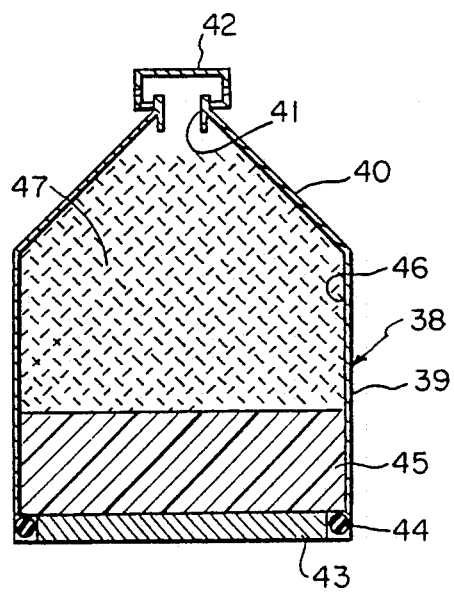
FIGS. 7 and 8 are views corresponding to FIGS. 5 and 6 of another embodiment of the invention.
Figure 8:
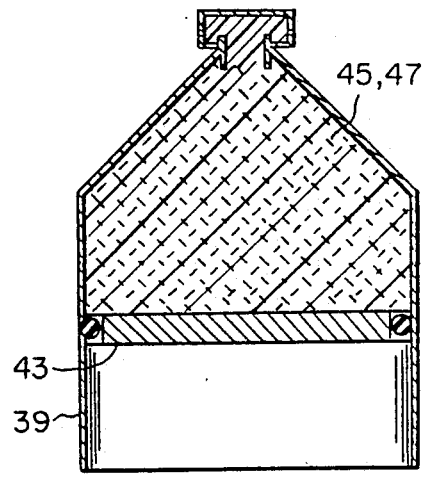

Referring to FIGS. 7 and 8 another embodiment of the invention is disclosed in which the container 38 is formed of a single piece having a cylindrical bottom 39 and conical top 40 with a filling opening 41 shown closed by a vented cover 42. The bottom portion 39 is open and has fitted thereon a piston 43 with a sealing ring 44. The bottom is filled with a volume of thermoplastic 45 of the type described above and the open space 46 above is shown filled (diagrammatically) with and array of waste items 47. A tension spring or other internal or external pressure means corresponding, for example, to the spring 37 of FIGS. 5 and 6 can be used. The filled container is then heated by, for example, an oven corresponding to the FIGS. 9 and 10 to drive the liquefied thermoplastic into the waste items, all as described above, to achieve the end result shown in FIG. 8.

Another embodiment of the invention is shown in FIG. 11 in which the container 48 is itself formed of the temperature-calibrated thermoplastic resin having a wall volume corresponding to the volume required to impregnate and encapsulate the waste items 49 contained therein. The container 48 is encased in a woven filamentary outer wrap 48a to contain and shield the liquid phase of the thermoplastic and the waste items 49. The filamentary wrap can impart deformability to the structure either in selected areas or throughout to allow the liquefied thermoplastic to be forced into the waste mass and, if desired, to adjust the container volume automatically to accommodate loads of different sizes and having different displacement characteristics. The wrap can be made puncture proof. It can also establish the pattern of change in the geometry between the treated and untreated unit to provide for the desirable visual verification of completion of sterilization.

Referring to FIG. 12 the entire sharps container 50 is formed from temperature-calibrated thermoplastic with no outer wrap or outer container. When filled with waste items 51 the container 50 with a vented cover 52, which can if desired be weighted, is dropped into a potting container 53 having tapering walls with a smooth parting surface formed for example of Teflon. The assembly is then heated in an oven to melt the thermoplastic container 50 to a sterilizing temperature of liquification at which time the gravity pressure causes encapsulation and impregnation of the waste items 51. When cooled and solidified the amorphous sterile mass is removed from the potting container 53 for disposal as environmentally safe material via conventional disposal means.

While the invention has been described having reference to preferred embodiments it will be understood that it can take other forms and arrangements. For example, the temperature calibrated thermoplastic compound can be materials other than plastic, so long as the material in its molten state is compatible with the temperatures required in the time/temperature death rate curve and has appropriate liquid and solid phases. It is also important that the molten material be brought into intimate contact with the contaminated waste material. In addition to the preferred embodiments herein disclosed it will be understood that this can be augmented by rolling, tumbling, shaking, vibrating, and air evacuation devices. Partial evacuation of the container can perform the manifold functions of aspirating waste gases, augmenting the flow of the liquid-phase plastic into all voids and of providing some or even all of the compression forces to cause the distortion of the container. This distortion forces the liquid into the mass of waste implements and, at the same time, provides for the easily viewed indication of successful completion of the sterilizing cycle. In the preferred embodiments the essential operational functions have been divided between the oven and the container. For example, the oven is the source of controlled heat as well as the pressure, i.e. the spring 21, to extrude the liquefied sterilizing medium into the mass of waste pieces. As disclosed, some or all of this pressure can be generated solely within the container itself by, for example, the internal spring 37 (FIGS. 5 and 6), the resilience of the base 18 (FIGS. 1-4) or the heat shrinking forces of certain plastics. It will be understood that it is possible to generate heat by different means such as chemically within the container itself or by means of microwave energy focused on the solid plastic. The latter can be rendered more susceptible to such heating by means of carbon dielectric fillers. It is also possible to establish more of the functions externally of the container by, for example, generating the liquefied sterilizing medium externally and injecting it into the waste filled containers, which can be partially evacuated to augment the liquid flow to create a void-free mass and which can also provide a force to deform the container to provide a visual indication that the process has been completed. The invention should not, therefore, be regarded as limited except as defined in the following claims.

I claim:

1. Apparatus for receiving, sterilizing and encapsulating medical implement wastes comprising
   a container having a waste receiving space and a volume of a normally solid thermoplastic compound having a temperature-calibrated melting point, and
   means to cause the compound in its heated liquid phase to flow into and around the mass of waste in said space to effect biological sterilization and, upon hardening, encapsulation of the waste items in a unitary solid mass.

2. Apparatus as set forth in claim 1 in which the temperature calibrated thermoplastic compound has a melting point at a temperature corresponding substantially to that which destroys biological life including spore forms on relatively brief contact, whereby the operation of the apparatus is rendered substantially free of unverifiable time constants subject to human error.

3. Apparatus as set forth in claim 1, said container including externally visible means to indicate when the temperature-calibrated thermoplastic compound has flowed into the waste space to penetrate and encapsulate the mass of waste items therein.

4. Apparatus as set forth in claim 1, including means to apply pressure to the temperature-calibrated compound in its liquid phase to cause it to flow into and around the mass of waste items.

5. Apparatus as set forth in claim 1 including vent means to exhaust air and vapor from the waste space during sterilization and encapsulation.

6. Apparatus as set forth in claim 1 including an overflow reservoir for excess liquid plastic carried by the container.

7. Apparatus as set forth in claim 1, said container being formed at least in part by said temperature-calibrated thermoplastic.

8. Apparatus as set forth in claim 7 including a filamentary reinforcement surrounding the container to maintain the integrity thereof during the liquid phase and to contain the waste items.

9. Apparatus as set forth in claim 7, the filamentary reinforcement affording deformability of at least part of the container to provide for visible geometric change to indicate completion of sterilization.

10. Apparatus as set forth in claim 7, including a potting container for the thermoplastic container.

11. Apparatus as set forth in claim 1, said container including at least a portion movable in direct proportion to the flow of the liquid phase thermoplastic compound into the waste mass.

12. Apparatus as set forth in claim 11 including resilient means to apply pressure to plastic compound to assist the flow in its liquid phase into the waste mass.

13. Apparatus as set forth in claim 11, the portion of the container containing the plastic compound being deformable and held by the plastic compound while in its solid phase in extended condition to define the space for the plastic compound prior to melting, said portion when deforming forcing the thermoplastic compound in its liquid phase into the waste mass and thereafter upon solidifying to hold the portion in its deformed condition.

14. Apparatus as set forth in claim 1, said container having a melting point substantially exceeding that of the plastic compound.

15. Apparatus as set forth in claim 11 including indicia on the container to indicate the hazardous mode prior to movement of the movable section and to indicate the safe mode thereafter.

16. Apparatus as set forth in claim 11, including, in combination, an oven to heat the container to liquefy the thermoplastic compound, and means in the oven to drive the movable portion of the container.

17. Apparatus as set forth in claim 16, said means to drive the movable portion of the container comprising a spring.

18. Apparatus as set forth in claim 16, including gaseous evacuation means in the oven coupled to the container to provide for functions selected from among aspirating waste gases, deforming the container and augmenting the flow of liquid phase thermoplastic to achieve a sterile, void-free mass.

19. A method for encapsulating and sterilizing medical implement wastes comprising the steps of
   (a) accumulating a supply of waste items in a container,
   (b) heating the container and a volume of thermoplastic compound having a calibrated melting temperature,
   (c) causing the molten plastic compound to flow around and among the waste items to fill all void spaces, and
   (d) solidifying the mass to create a biologically sterile mass in which all sharp edges and points are encapsulated against external exposure.

20. The method as set forth in claim 19 in which the melting point of the temperature-calibrated thermoplastic compound corresponds to the temperature at which all biological life, including spore forms, is rendered sterile substantially on contact.

* * * * *